(12) United States Patent
Platt

(10) Patent No.: US 7,491,708 B1
(45) Date of Patent: Feb. 17, 2009

(54) MODIFIED PECTIN

(76) Inventor: David Platt, 12 Appleton Cir., Newton, MA (US) 02459

( * ) Notice: Subject to any disclaimer, the term of this patent is extended or adjusted under 35 U.S.C. 154(b) by 0 days.

(21) Appl. No.: 08/024,487

(22) Filed: Mar. 1, 1993

(51) Int. Cl.
*A61K 31/715* (2006.01)

(52) U.S. Cl. .................. 514/54; 536/123.1; 536/124; 536/126; 536/127; 435/32; 435/101

(58) Field of Classification Search ............ 435/32, 435/101; 436/63, 64; 536/2, 80, 123.1, 124, 536/126, 127; 514/54; 425/32, 101
See application file for complete search history.

(56) References Cited

U.S. PATENT DOCUMENTS

| | | | |
|---|---|---|---|
| 2,444,266 A | 6/1948 | Owens et al. | ................. 195/30 |
| 4,016,351 A | 4/1977 | Eschinasi | ................. 536/2 |

FOREIGN PATENT DOCUMENTS

| | | | |
|---|---|---|---|
| DE | 143 261 | | 8/1980 |
| DE | 143261 | | 8/1980 |
| JP | 39039C22 | | 4/1980 |
| JP | 39039C/22 | * | 4/1980 |
| JP | 88 51 50094/22 | | 4/1988 |
| JP | 88-150094/22 | * | 4/1988 |
| JP | 88515009422 | | 4/1988 |

OTHER PUBLICATIONS

Platt et al, *Journal of the National Cancer Institute*, vol. 84, No. 6, Mar. 18, 1992.*
Mueller et al, *Chemical Abstracts*, vol. 110, p. 44, Ref. # 165780g, 1989 (Immunopharmacology 1989, 17(1), 11-18).*
Hosoda et al, *Chemical Abstracts*, vol. 110, p. 635, Ref. #6827 m, 1989.*
Neff et al, *Plant Physiol.*, vol. 83, pp. 525-528, 1987.*
Curti, *Critical Reviews on Oncology/Hematology*, vol. 14, pp. 29-39, 1993.*
Osbaud et al, *Immunology Today*, vol. 11, No. 6, pp. 103-105, 1990.*
Trott, "Differences between mouse and human tumors that effect their responses to radiotherapy" Edited by Kullman, *Pregamon Press*, pp. 6-11, 1987.*
Seiman, Satisfactory and Unsatisfactory tumor models Factors influencing the selection of a tumor model for experimental evaluation; Edited by Kullman, *Pergamon Press*, pp. 12-15, 1987.*
Jain, *Scientific America*, pp. 58-65, Jul. 1994.*
Fidler, *Cancer Research*, vol. 35, pp. 218-224, 1975.*
Dumont et al, *Cancer Research*, vol. 52, pp. 1195-1200, Mar. 1, 1992.*
Schultz et al, *Cancer Research*, vol. 48, pp. 5539-5545, Oct. 1, 1988.*
Finne et al, *Int. J. Cancer*, vol. 43, pp. 300-304, 1989.*
Devita et al., Cancer: Principles & Practice of Oncology, 5th edition, Chapter 7, pp. 139, 143-146 (1997).*
Beuth et al. Clin. Expl. Metastasis (1988), vol. 6, pp. 115-120.*
Journal of the National Cancer Institute, vol. 84, No. 6. Mar. 18, 1992; Platt et al. "Modulation of the Lung Colonization of B16-F1 Melanoma Cells by Citrus Pectin".

* cited by examiner

*Primary Examiner*—Patrick T Lewis
(74) *Attorney, Agent, or Firm*—Greenberg Traurig, LLP

(57) ABSTRACT

A modified pectin consists essentially of neutral sugar sequences with a low degree of branching capable of preventing tumor cell migration and cell to cell and cell to substratum adhesion.

10 Claims, 8 Drawing Sheets

β-ELIMINATION NaOH pH 10.0

HCl pH 3.0

MODIFIED PECTIN

TECHNICAL FIELD

The present invention relates to a chemotherapeutic agent and a method of using the same for inhibiting malignant metastasis. More specifically, the present invention relates to a modified pectin capable of inhibiting tumor cell motility and tumor cell to cell and cell to substratum adhesion.

BACKGROUND ART

Scientists have determined a close correlation between tumor cell surface receptors and metastasis. Metastasis is the transfer of neoplastic disease from one organ or part of an organ to another organ, the two organs not being directly connected. For example, the transfer of a melanoma from one tissue to the lung or liver. It has been determined that the process of metastasis is initiated by the detachment of tumor cells from the primary growth situs and is followed by the invasion by these detached tumor cells in surrounding tissues and blood vessels. The tumor cells disseminate in the blood circulation to distant organs where the tumor cells arrest and proliferate to form new tumor colonies. (1).

Cell surface constituents, such as glycoproteins, have been implicated in the mediation of cellular interactions related to recognition, adhesion, growth, differentiation and morphogenesis. (2) Cell adhesiveness which plays a roll in normal morphogenesis and homeostasis is also an important factor in the pathogenesis of cancer (3). For example, the copending European Patent Application PCT/EP 85/00557 to Max-Planck-Gesellschaft Zur Fo-rderung Der Wissenschaften E.V. discloses specific carbohydrate binding proteins of mammalian tumor cells which specifically recognize and bind to carbohydrate molecules on the cell surface of mammalian tumor cells. These lectins have been used for diagnostic purposes to detect mammalian tumor cells and are proposed as a pharmaceutical composition for treating malignant neo-plasms by inhibiting metastasation.

It has been shown that intercellular recognition and adhesion among tumor cells and host cells lead to the formation of tumor cell emboli, the formation of the emboli being correlated to the incidence of metastasis (4). Accordingly, intercellular recognition receptors on cell surfaces bound by an antigenic component should inhibit the formation of tumor cell emboli thereby inhibiting metastasis.

For example, when B16-F1 melanoma cells were cultured as spheroids on a non-adhesive substrate (5), the cells showed an increased propensity to colonize in the lungs of C57BL/6 mice in a reversible manner. This was found to be correlated to the increased expression of a cell surface sialylated Peanut Agglutinin (PNA) binding glycoprotein, gp78 (6). Pretreatment of the cells with polyclonal anti-gp78 antibodies prior to intravenous injection in sygenic mice induced an effect similar to that of altered cell shape growth conditions, the treated cells exhibiting a two fold increase in lung colonization. This result suggested a role for the gp78 molecule in metastasis (7).

As stated above, the molecular nature of the cell surface proteins, including certain carbohydrate-binding-proteins (CBP) mediate such cognitive cellular interactions, and their role as tumor surface lectins in anchorage independent growth in vitro and in tumor embolization and heterotypic aggregation during the metastatic process in vivo has been suggested (8-10). For example, the presence of lactose binding lectin in various murine and human tumor cells has been described (11-13). Quantitative analysis of tumor cell arrest and survival has shown that most of the intravenously inoculated tumor cells are initially trapped in the first capilliary bed encountered by the cells, that being lung tissue (14). Complimenting this finding is the finding that isolated tumor cells rarely lead to hematogenous metastasis of tumors (15). Further tumor emboli are predominantly responsible for tumor dissemination and arrest at secondary sites (16). The importance of tumor cell aggregation has been further demonstrated by the correlation established between the propensity of tumor cells to undergo homotypic aggregation or to participate in heterotypic aggregation in vitro and their metastatic potential in vivo (17). It is further assumed that the specific arrest of tumor emboli in particular organs requires cognitive interactions between the tumor cells and post capilliary endothelial cells of the basement membrane (18, 19).

Researchers have reported on the involvement of carbohydrate residues in the mediation of adhesion between cells and the ability of simple sugars, glycopeptides and glycoproteins to inhibit the aggregation of certain types of cells (20). In other words, simple sugars have been shown to prevent cell to cell aggregation. Another report shows that fucosyltransferase from human milk immobilized on polystyrene plates enhances the adhesion of cells by binding cell surface oligosaccharide acceptors. This adhesion can be inhibited by oligosaccharides containing the sugar sequence galactosyl (beta-1-4)N-Acetylglucosamine (21).

With regard to function of glycolipids on the cell surface, studies on the adhesion of liposomes containing various glycolipids to Hella cell carcinomas as a model of Hella cell membrane function demonstrated, that the glycolipids containing terminal galactose residues were the most active in promoting adhesion (22), and the fundamental role of a 34 KD, a galactoside binding lactin 34,000 in cell transformation and metastasis has been demonstrated (11-13).

Most cell types contain lectins of different molecular weights and different sugar specificities including lactosides, mannose and fucose. In general, different types of lectins have different cellular compartments (23).

Finally, the absorption of the *Agrobacterium Tumefaciens* strain B6 was increased if citrus pectin, polygalacturonic acid or demethylated pectin was included in the inoculum (24). In another study it was shown that the administration of citrus pectin in vivo resulted in a high incidence of colorectal tumors (25).

The present invention provides a modified citrus pectin able to affect motility of malignant tumor cells and prevent lung colonization in vivo.

SUMMARY OF THE INVENTION

In accordance with the present invention, there is provided a modified pectin consisting essentially of neutral sugar sequences with a low degree of branching capable of preventing tumor cell migration and cell to cell and cell to substratum adhesion.

The present invention further provides a modified pectin made by the process of depolymerizing the pectin polymer by interrupting the rhamnogalacturan backbone of the pectin molecule and then breaking down the side chains of neutral sugars into oligimers of neutral sugars having a molecular weight of about 10.2 as measured by viscosity measurements at 26° C.

Further the present invention provides a method of immobilizing tumor cells and inhibiting cell to cell and cell to substratum adhesion, the method including the steps of treating tumor cells with a modified pectin consisting of neutral sugar sequences with a low degree of branching and binding the modified pectin to tumor cell receptors. The receptors are inhibited from interacting with other cells and substratum.

BRIEF DESCRIPTION OF THE DRAWINGS

Other advantages of the present invention will be readily appreciated as the same becomes better understood by reference to the following detailed description when considered in conjunction with the accompanying drawings wherein.

DETAILED DESCRIPTION OF THE DRAWINGS

In accordance with the invention there is provided a modified pectin consisting essentially of neutral sugar sequences with a low degree of branching capable of preventing tumor cell migration and cell to cell substratum adhesion. More specifically, the modified pectin has a molecular weight of about 10.2 as measured by viscosity measurements at 26° C. as set forth below.

Figure 6A:
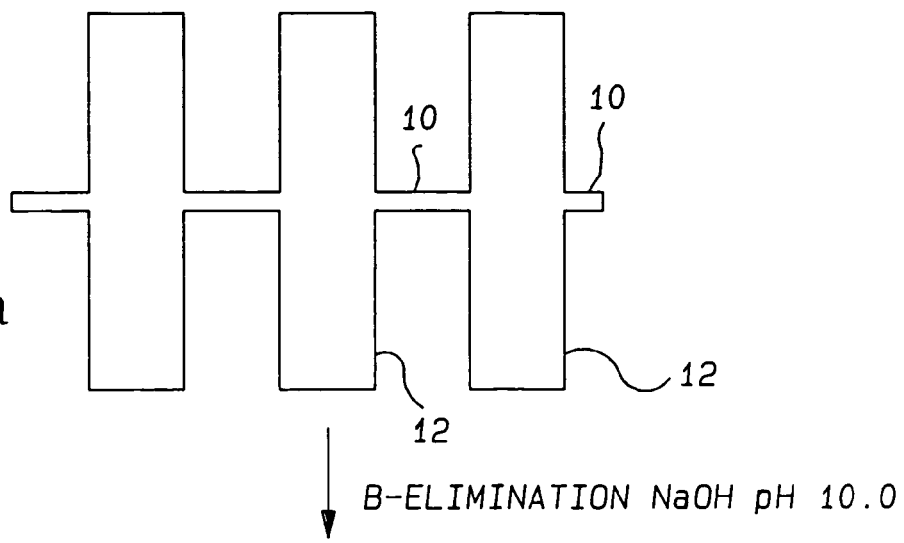
FIGS. 6a.-6c. show schematically the depolymerization mechanism of pectin polymer.
Figure 6B:
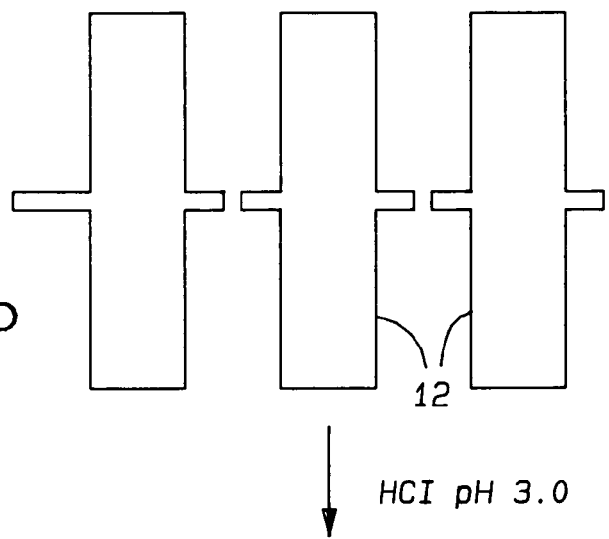
Figure 6C:
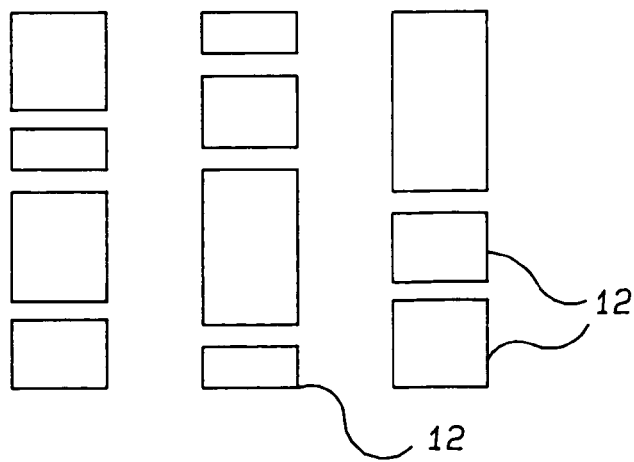
Figure 7:
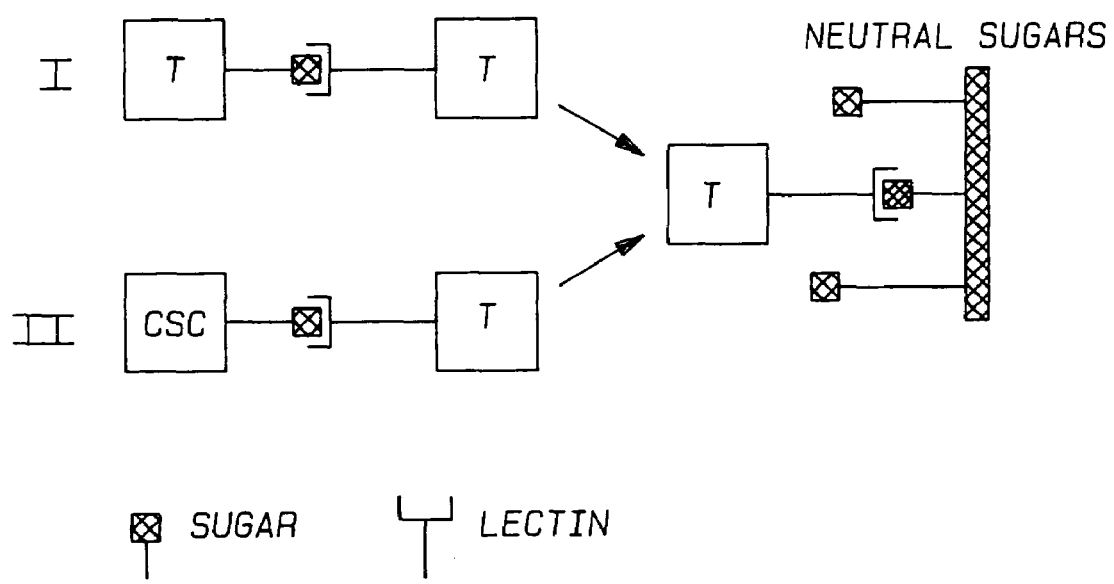
FIG. 7 shows the mechanism by which neutral sugars from group B mediated intercellular adhesive interactions. T-tumor cell. CSC-Cell surface carbohydrates on certain normal host cells.

A specific example of a modified pectin made in accordance with the present invention is a modified citrus pectin as illustrated in FIG. 6. The modified pectin is generally made by the process by first depolymerizing the pectin polymer by disrupting the rhamnogalacturan backbone of the pectin molecule indicated schematically at 10 in FIG. 6a. This depolymerization step can be accomplished by pretreating the pectin with a high pH solution. That is, the pectin can be dissolved in an aqueous solution and the pH of the solution raised to above 10.0. The basic conditions eliminate the backbone 10. Next, the side chains of neutral sugars, generally shown at 12 in the schematic representation of FIG. 6a, are broken down into smaller low branched sugars 12' as shown in FIG. 6c. These sugars 12' are of neutral sugars having an average molecular weight of about 10.2 as measured by viscosity measurements at 25° C. as set forth below. This breaking down step can be accomplished by treating the depolymerized pectin with a low pH solution. That is, once the dissolved pectin is exposed to the sodium hydroxide at approximately a pH of 10, the pH of the solution is then adjusted to approximately 3.0 until the pectin breaks down to the molecular weight of about 10.2. The solution is then neutralized to a pH of about 6.3. The pectin is then washed and dehydrated to a final solution of about 5-10 percent by weight. Of course, this can be varied depending upon the clinical situation.

The following data demonstrates a method of using the modified pectin made in accordance with the present invention for immobilizing tumor cells and inhibiting cell to cell and cell to substratum adhesion resulting in the inhibition of metastasis of the tumor cells. Generally, this is obtained by first treating the tumor cells with the modified pectin consisting of the neutral sugar sequences with a low degree of branching and binding the modified pectin to tumor cell surface receptors. The receptors are inhibited from interacting with other cells and the substratum.

EXPERIMENTAL EVIDENCE

Materials and Methods

Modified Citrus Pectin (MCP).

Citrus Pectin 0.5% from Sigma Co., 10% Methoxyl groups, was treated under U.V. radiation for 48 hours. The pectin solution was prepared under sterile conditions. The pectin was slowly dissolved in distilled water. The amount of total carbohydrate was determined by the phenol sulfuric acid method (27). The pH of the pectin solution was increased to pH 10.0 with NaOH 3N for 30 minutes and then decreased to pH 3.0 with HCL 3 N. After 10 and 24 hours, samples were taken and the pH of the samples was equilibrated to pH 6.3 and the solutions were washed with ethanol 70% and dried with acetone 100%. Samples of dried pectin were taken and rehydrated with PBS to a final solution of 0.5% and mixed gently with the B16-F1 tumor cells.

Preparation of Asialofetuin.

Fetuin from Gibco laboratory hydrolysed in 0.05 N sulfuric acid at 80° C. for one hour. The released sialic acid was removed from the fetuin by dialysis.

Molecular Weight.

The molecular weights of citrus pectin and MCP were determined by viscosity measurements (30), at 26° C. in an Ubbelohde No 1 viscometer with CMF/PBS 20 mM pH 6.2, EDTA 0.2% and NaCl 0.1 N. Intrinsic viscosity (n) was obtained by extrapolating the specific concentration values obtained to zero galacturonic acid concentration.

Quantities of Neutral Sugars from Citrus Pectin.

Total neutral sugars were estimated from the difference between the m-hydroxyphenol method (22) and the total carbohydrate with phenol sulfuric acid (28). The composition and the amount of individual neutral sugar was obtained by hydrolysis in trifluoroacetic acid (2N). The respective alditol acetates were analyzed by gas chromatography (28).

More specifically, Citrus' Pectin from Sigma Company was used having 10. % methoxyl groups. The amount of anhydro-galacturonic acid (AGA) was determined by the m-hydroxlyphenol method (26) and for total carbohydrate by reaction with phenol-sulfuric acid (27). Total neutral sugars were estimated from the difference between the two reactions based on galacturonic acid and glucose standards. The composition and the amount of individual neutral sugar was obtained by hydrolysis in trifluoroacetic acid (2N). The respective alditol acetates were analysed by gas chromatography (28).

Tumor Cell Lines

The B16-F1 line (low incidence of lung colonization) was derived from pulmonary metastasis produced by intravenous injection of B16 melanoma cells (31). The cells were grown in a monolayer on plastic in Dulbecco's modified Eagle's minimal essential medium supplemented with glutamine, nonessential amino acids, vitamins, antibiotics and 10% heat-inactivated fetal bovine serum (FCS 10%). The cells were maintained at 37° C. in a humidified atmosphere of 7% $CO_2$, 93% air. To ensure reproducibility, all experiments were performed with cultures grown for no longer than six weeks after recovery from frozen stocks.

Monoclonal Antibody Against gp 78.

The 3F3A mAb was generated as previously described by others (32). Lewis rats were immunized with a PNA affinity column eluate of sialidase (Calbiochem, Calif.) treated B16-F1 membranes which contained desialylated gp 78 (7). The spleen of the immunized rat was fused with NSO myeloma cells (obtained from Dr. Zelig Eshhar, Weizmann Institute of Science, Rehovot, Israel). Positive hybridomas were selected by immunoblot recognition of gp 78 yielding the 3F3 clone which was subcloned to give the 3F3A monoclonal hybridoma. The 3F3A mAb was determined to be of IgM subclass by an Ouchterlony test. Ascites fluid was generated from the i.p. injection of irradiated CB6-F1 mice. A purified IgM fraction was prepared from 3F3A ascites fluid by affinity chromatography on a Protein A Sepharose column (Beckman, Ill.) followed by gel filtration on Sephacryl 300 (1×90 cm, Pharmacia, Sweden).

Phagokinetic Track Motility Assay

Uniform carpets of gold particles were prepared on coverslips coated with BSA, as described by others (9). Colloidal gold coated coverslips were placed in 35 mm tissue culture dishes containing 2 ml medium supplemented with antibodies 3F3A, B16-F1 conditioned media (FCS 10%) and 200 B16-F1 cells grown in monolayer or suspension culture were added to each plate. After 24 hours, phagokinetic tracks were visualized using dark field illumination in an Olympus or Nikon inverted microscope at a magnification of 200×. The area cleared of gold particles by at least 50 cells was measured using a video plan image analysis system (Carl Zeiss, Thornwood, N.Y.). The standard error reflecting a 95% confidence level was calculated.

Assay of Pectin-Induced Homotypic Aggregation

Cells were detached with 2 mM EDTA in CMF-PBS and suspended at $1×10^6$ cell/ml in CMF-PBS with and without 0.05% Pectin and 0.05% modified Pectin. Aliquots containing 0.5 ml of cell suspension were placed in siliconized glass tubes and agitated at 50 rpm for 30 min at 37° C. The aggregation was then terminated by fixing the cells with 1% formaldehyde in MF-PBS. Three samples were used for counting the number of single cells by using a hemacytometer, and aggregation was calculated according to the equation:

$$(1-N_t/N_c)\times 100$$

where Nt and Nc represent the number of single cells in the presence of the tested compounds and the number of single cells in the control buffer (CMF-PBS), respectively.

Lung Colonization Assay

Unanesthetized female C57BL/6 mice, 8 weeks old, were inoculated i.v. in the tail vein with $1×10^5$ tumor cells in 0.2 ml PBS. After 17 days the mice were autopsied and their lungs were removed, rinsed and fixed with 5% formaldehyde in PBS. The number of tumor colonies in the lungs were determined under a dissecting microscope.

More specifically, in one experiment, unanesthetized female C57BL/6 mice (n–6), being 8 weeks old, were inoculated i.v. in the tail vein with $1×6^5$ tumor cells in 0.2 m. solution of Calcium Magnesium free PBS (CMF/PBS) and Citrus Pectin. The Citrus Pectin Solution was prepared as described above. Mice were sacrificed at 17 days post injection and the nodules per lung were measured under a dissecting microscope.

In a separate set of experiments unanesthetized female C57BL/6 mice that were 8 weeks old were inoculated i.v. in the tail vein with $1×10^5$ tumor cells in 0.2 ml CMF/PBS solutions of modified pectin. The mice were sacrificed at 17 days post injection and the nodules per lung were measured under dissecting microscopes. The modified pectin was made as follows:

1. (A) MCP 0.5% was prepared by increasing the pH of the pectin solution to pH 10.0 in NaOH 3 N for thirty minutes and then the pH was decreased to pH 3.0 with HCl. The pectin solution was kept at that pH for 15 minutes. Then the pectin solution was neutralized to pH 6.3. The solution was washed with ethanol 70% and dried with acetone 100%.

2. (B) MCP 0.5% was prepared as (A) MCP but the pectin solution was kept at pH 3.0 for 10 hours.

3. (C) MCP was made by a dilution of 1:10 of (B) MCP solution.

4. (D) MCP 0.5% was prepared as (A) MCP but the pectin solution was kept at pH 3.0 for 24 hours.

RESULTS

Figure 1:
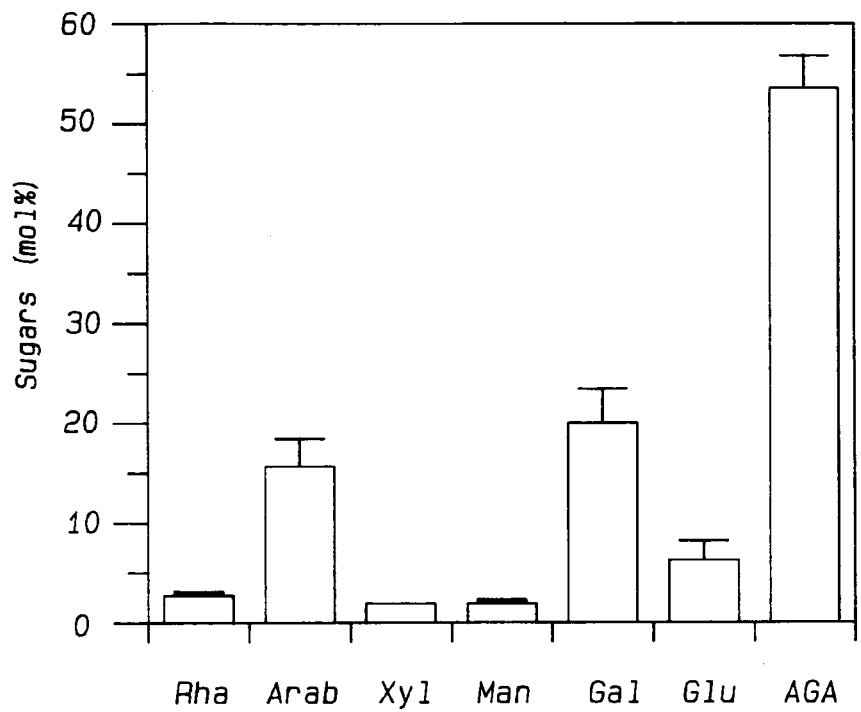
FIG. 1 shows the sugar composition of citrus pectin (mole %)

Pectin is a polysaccharide responsible for the texture of fruits and vegetables in nature. The substance consists generally of chains of partially esterified galacturonic residues with side chains composed or arabinose galactose and xylose. As shown in FIG. 1, the sugar composition exhibited a hydrogalacturonic acid content of 54%. Galactose and arabinose were found to be 36% of the composition from the total sugars and 78% from the total neutral sugars.

Figure 2A:
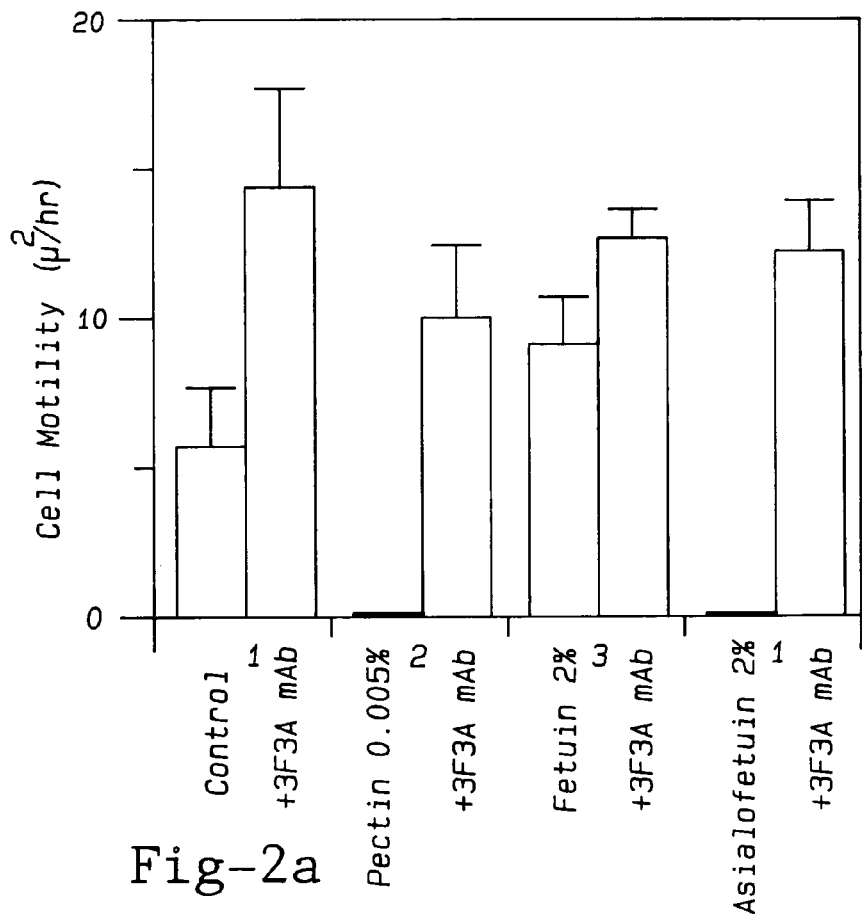
FIG. 2a shows motility of B16-F1 cells plated on colloidal gold cover slides.
Figure 2B:
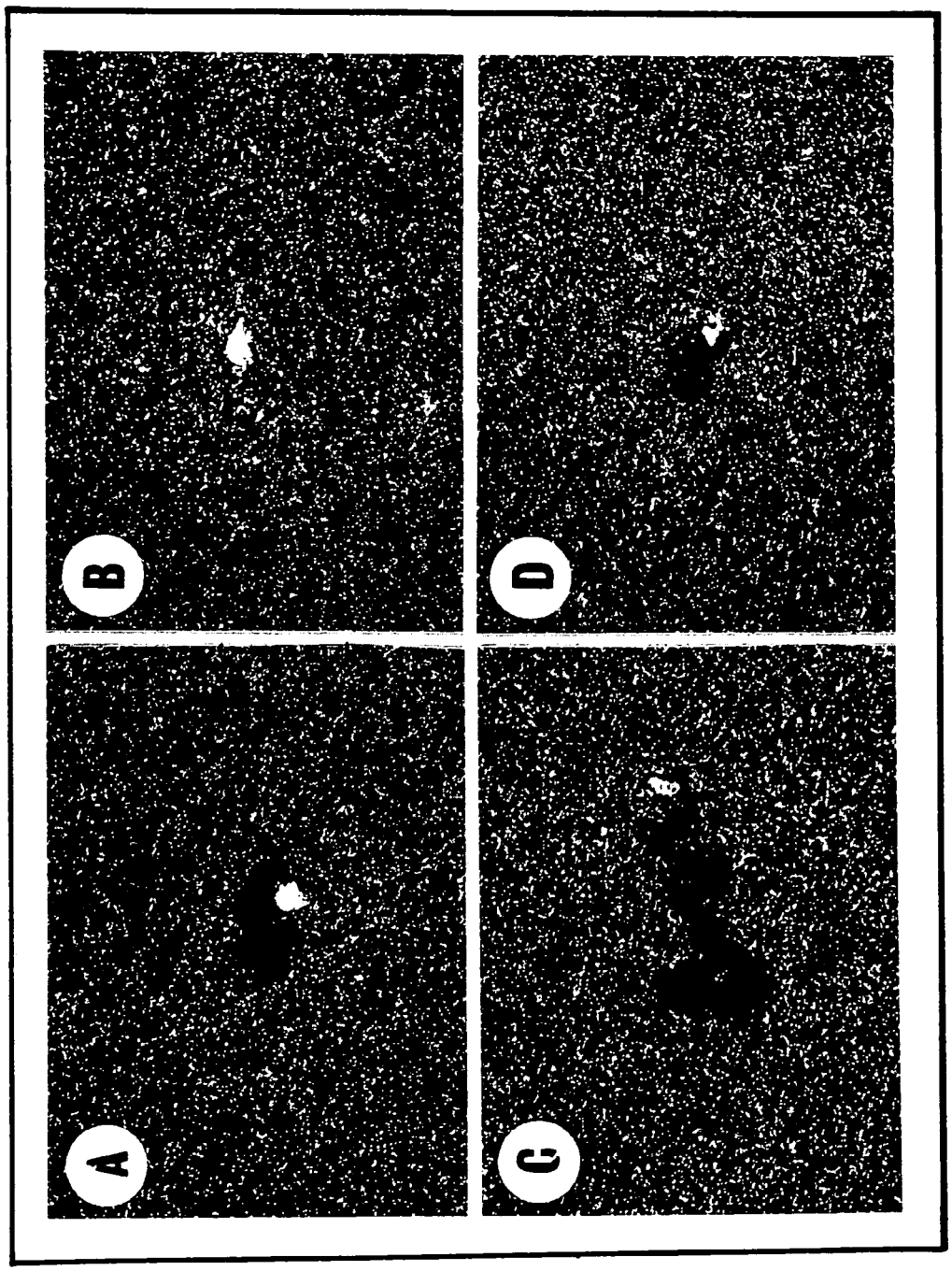
FIG. 2b is a series of photomicrographs, labeled A-D, showing motility of B-16-F1 cells plated on colloidal gold coated slides.

The results of the motility tests of B16-F1 cells is illustrated in FIGS. 2a and 2b. These tests indicate the influence of the citrus pectin on locomotor activity. The B16-F1 cells exhibited no Phagokinetic tracks when the slide was covered with $5×10^{-3}$% pectin or asialofetuin 2%. When the slide was covered with BSA 1% as a control or fetuin 2% the phagokinetic tracks produced by the B16-F1 cells were $5.9^{\pm}1.3$ μg/hr and $8.72^{\pm}$ μg/hr respectively.

To determine if gp78 plays an active role in cell movement when the slides were coated with pectin, the effect of the 3F3A mAb on cell motility was assayed. B16-F1 cells plated on gold particle coated with BSA 1% exhibited $14.26^{\pm}3.6$ μg/hr phagokinetic tracks compared to $9.7^{\pm}2$ μg/hr in tracks areas, with the presence of pectin on cover slides, as further illustrated in FIGS. 2a and 2b.

In the presence of fetuin or asiallofetuin on cover slides, the motility was negligible. In the presence of 3F3A mAb (10 μg/ml) motility was similar as shown in FIG. 2a.

Figure 3:
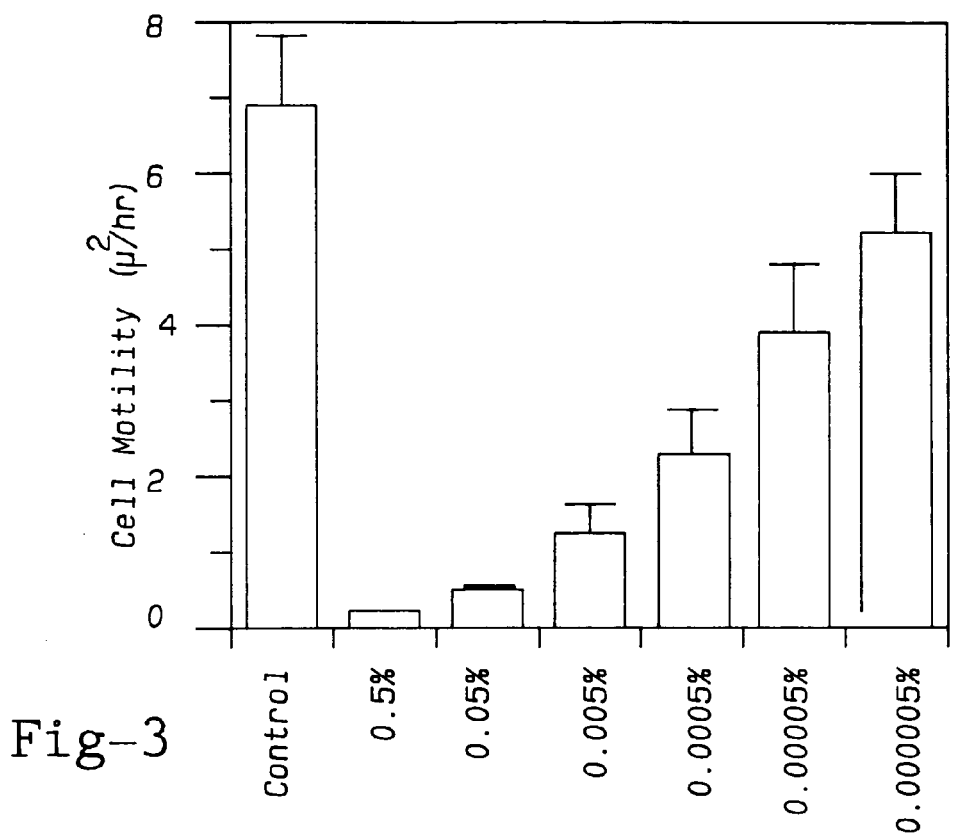
FIG. 3 shows motility inhibition of B16-F1 cells plated on colloidal gold cover slides.

The exposure of pectin on the cover slides exhibited a decrease in cell motility of $5×10^{-6}$% pectin, as shown in FIG. 3.

Figure 4:
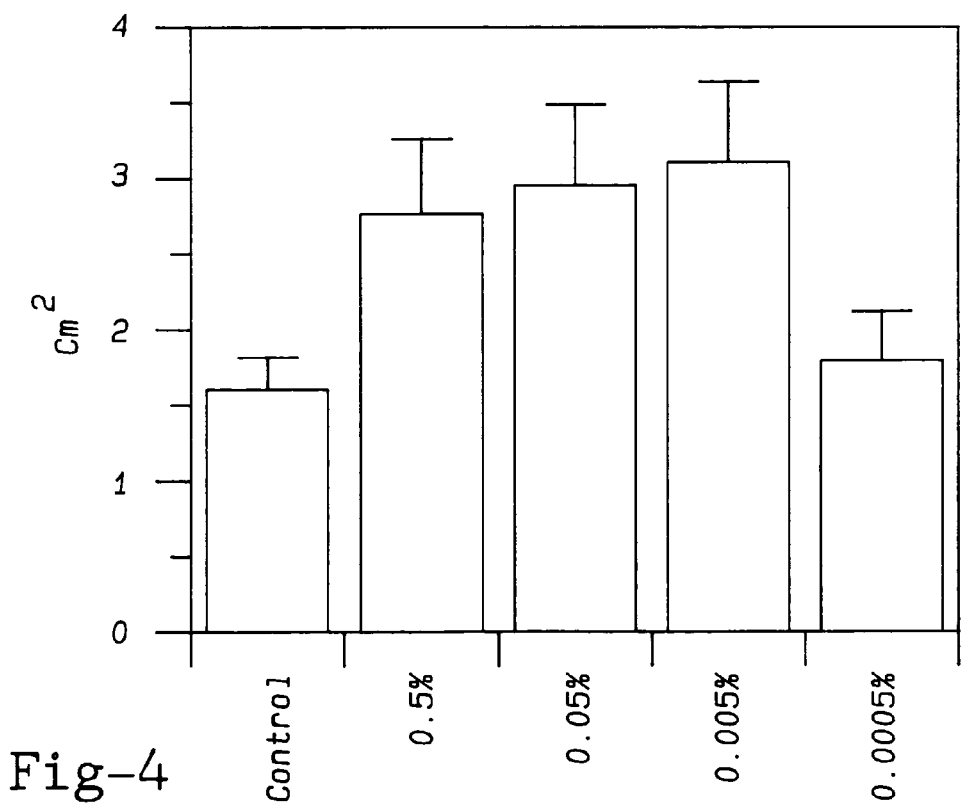
FIG. 4 shows experimental metastasis after subcutaneous (S.C.) injection of B16-F1 cells ($1 \times 10^5$) with citrus pectin.
Figure 5:
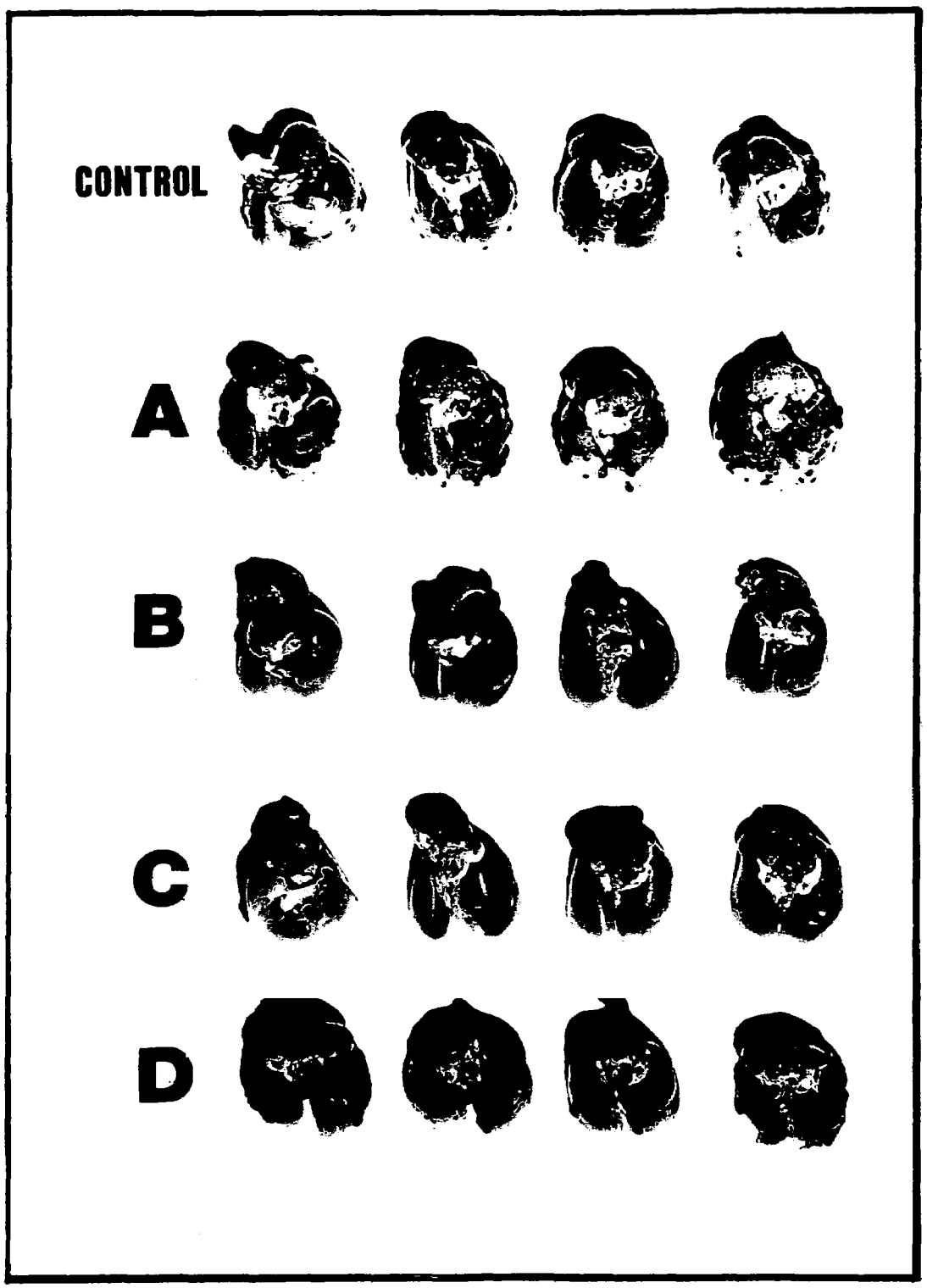
FIG. 5 is a photomicrograph showing a control group, and for experimental groups (A-D) of mouse lungs from experimental pulmonary metastasis after injection of B16-F1 cells ($1 \times 10^5$) with MCP.

The effect on metastasis in vitro in the presence of citrus pectin is shown in FIGS. 4 and 5 and illustrated in Tables 1 and 2. There was no cytotoxic effect on the B16-F1 melanoma cells when the cells were treated with 0.05% pectin. The growth rate of these cells was normal compared to control. Subcutaneous (s.c) injection of mice with concentrations of pectin resulted in the data shown in FIG. 4. The s.c. injection of the various concentrations of pectin exhibited an increase in size of the s.c. tumor of about two-fold. The comparison was 1.6+0.91 cm² in the control compared to 2.8-3.2 cm² between 5×10⁻¹% and 5×10⁻³% pectin. Only when the cells were exposed to 5×10⁻⁴% pectin as shown in FIG. 4, the size of the subcutaneous tumor was similar to the control. No tumors were found in the lungs or in other parts of the mice body. As illustrated in the Figures, each value of the subcutaneous tumor size represents the average±the standard error of 12 mice in two different experiments.

To examine whether pectin has any effect on the ability of B16-F1 cells to form colonies in the lungs, a mixture of melanoma cells and various concentrations of pectin were injected intravenously to mice. After 17 days, the mice were autopsied and the number of nodules in the lungs were counted, the data being set forth in Table 1. More specifically, unanesthetized female C57BL/6 mice (8 weeks old) were inoculated intravenously in the tail vein with 1×10⁵ tumor cells in 0.2 ml solution of calcium magnesium free PBS and citrus pectin. The citrus pectin solution represented as % was prepared accordingly as set forth above. Mice were sacrificed at 17 days post injection and the nodules per lung were measured under a dissecting microscope.

There was a three-fold increase compared to the control after the B16-F1 cells were treated with pectin as set forth in Table 1. Only the 5×10⁻⁵% pectin exhibited approximately the amount of nodules in the lung compared to the control.

TABLE I

| Group | No. | Lung Nodules Range[a] | Mean | p[b] |
|---|---|---|---|---|
| Control | 12 | 6-126 | 43 | $p < 0.001$ |
| $5 \times 10^{-1}$ | 9 | 68-172 | 139 | $p < 0.01$ |
| $5 \times 10^{-2}$ | 12 | 52-154 | 112 | $p < 0.1$ |
| $5 \times 10^{-3}$ | 10 | 18-120 | 80 | $p < 0.001$ |
| $5 \times 10^{-4}$ | 10 | 34-182 | 80 | $p < 0.025$ |
| $5 \times 10^{-5}$ | 12 | 19-102 | 74 | $p < 0.01$ |

[a]Metastasis was observed in 100% of the mice.
[b]Significantly different from each group by Mann Whitney test.

To evaluate these findings further, the B16-F1 cells were exposed to various modified citrus pectin prior to injection. The (A) MCP exhibited an increased number of nodules in the lung as set forth in Table 2 and shown in FIG. 5. The (B) MCP exhibited no presence of nodules in the lung. A 1:10 dilution of the (B) MCP labelled (C) MCP exhibited the presence of 0-1 nodules in the lung. The (D) MCP exhibited approximately the number of nodules in the lung compared to the control.

TABLE II

| Group | No | Lung Nodules Range | Mean | Mw |
|---|---|---|---|---|
| Control | 43 | 10-47 | 33[a] | |
| A | 41 | 78-134 | 101[b] | 82.0 |
| B | 42 | 0 | — | 10.2 |
| C | 40 | 0-1 | — | |
| D | 39 | 18-105 | 49[c] | 4.0 |

[a]Significantly different from other groups p < 0.001, Mann Whitney Test.
[b]Significantly different from control (p < 0.001), and from group 0 (p < 0.01).
[c]Significantly different from control and group A p < 0.001.

Figure 8:
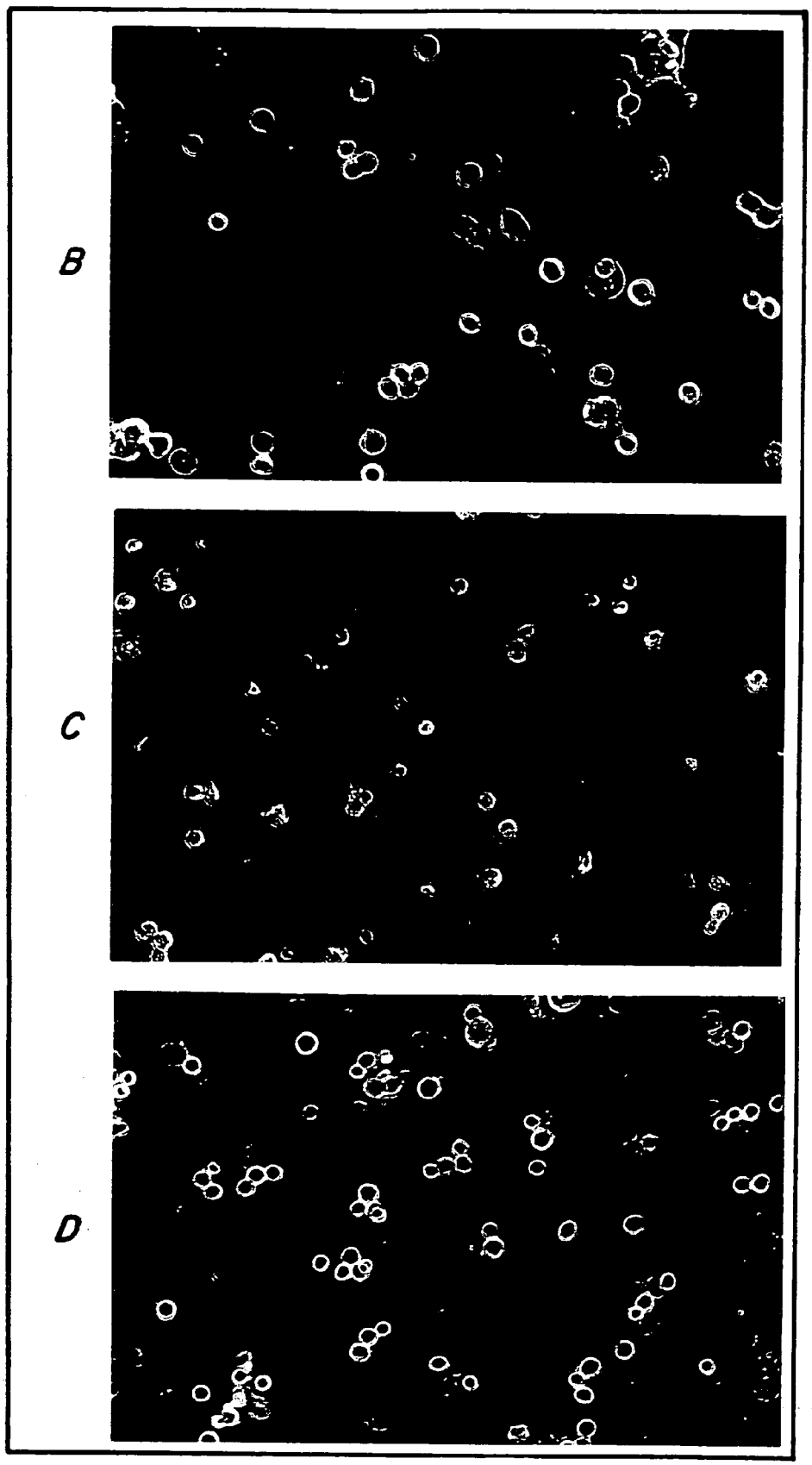
FIG. 8a. is a graph illustrating results of an experimental series measuring the percent aggregation of tumor cells in vitro for a control group, a group of cells containing pectin, and a group of cells containing the modified pectin of the present invention.
FIGS. 8b.-8c. are photomicrographs of the cells from the experimental series of FIG. 8a. with FIG. 8b. illustrating the control cells, FIG. 8c. illustrating the pectin containing cells and FIG. 8d. illustrating the modified pectin containing cells.
Figure 8A:
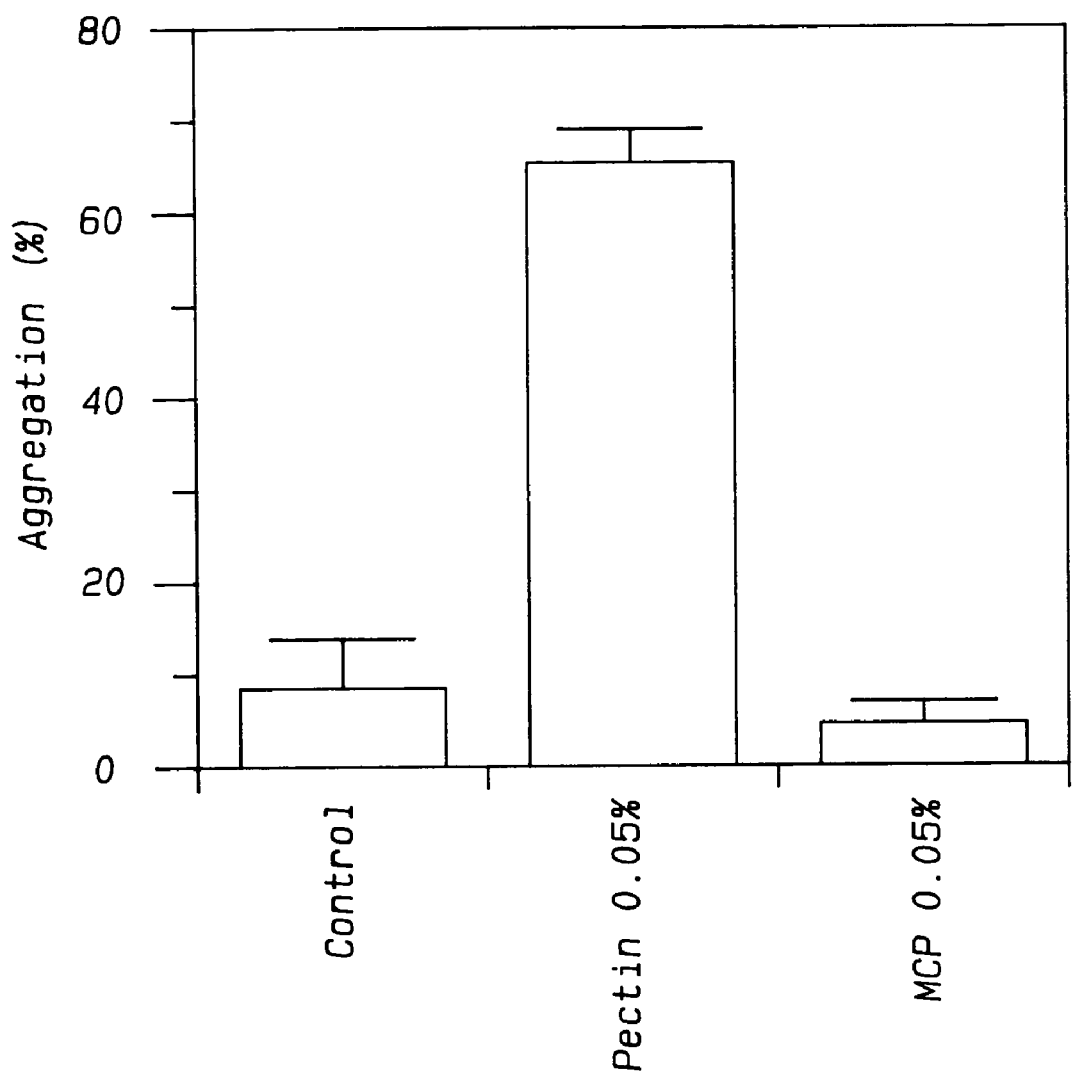

As shown in FIG. 8(A), pectin 0.05% greatly induced tumor cell aggregation in vitro which MCP 0.05% significantly reduced aggregation. As shown in FIGS. 8(B)-(D), after cells were agitated for 30 minutes at 37° C. and then photographed using a phase-contrast inverted microscope, cells in the presence of pectin 0.05% aggregated (8C) to a significantly greater extent than control. Cells in the presence of MCP 0.05,% (FIG. 8C) aggregated significantly less than control (FIG. 8B).

DISCUSSION OF EXPERIMENTAL RESULTS

Because the detachment of tumor cells from the primary growth site is a necessary preliminary step for metastasis, the motility phenomena also has importance in understanding the metastasis process while the tumor cells are in the circulation. The arrest of some of the cells in organs is influenced greatly by the formation of tumor emboli resulting from interaction of the metastatic cells with other tumor cells, homotypic aggregation, and with circulating host cells, heterotypic aggregation, such as lymphocytes (35, 36).

The aggregation probably occurs because of the galactoside-specific hemagglutinating activity presence in neoplastic cells and it was demonstrated in murine neuroblastoma cell extract (32). Therefore motility and aggregation are important factors related to metastasis of tumors.

The tumor cell surface lectin involvement in cell to cell interaction comes from the phenomena that fetuin and its desialylated derivatives bind to the surface of tumor cells and mediate their homotypic aggregation in vitro (38).

The cell surface lectins recognize and bind galactosyl residues on different side chains of the asialofetuin molecule (38). The glycoprotein could serve as a cross-linking bridge between adjacent cells and form aggregates. The binding of fluorescent derivatives of the fetuin was greatly reduced by 4-O-β-D-galactopyranosyl-D-glucose (38). The fetuin molecule consists of a single polypeptide chain, to which three complex heteropolysaccharide side chains made up of sialic acid, galactose, N-acetyl-D-glucosamine and mannose are attached through asparagine residues and as well as 3-O-glycosidically linked units composed of sialic acid galactose, and N-acetyl-D-galactosamine (39).

Pectin is a structural cell wall polysaccharide of all higher plants. The substance is primarily a polymer of D-galacturonic acid. The principal of all pectin molecules is a linear chain of (1-4)-linked α-D-galactopyranosyluronic acid units. Some of the carboxyl groups are in the methyl ester form. Neutral sugars, primarily L-rhamnose, are also present. In citrus pectin (40) L-rhamnopyranosyl units are inserted into the galacturonan chain in the following manner O-α-D-GalpA-(1-2)-D-L-Rhap-(1-4)-O-α-D-GalpA. The configuration of the L-rhamnopyraanosyl linkage is unknown, but the calculations have shown that is it is beta configuration (40). The L-rhamnopyranosyl units are distributed within the galacturonan backbone (41, 42), and it was reported (42) that apple pectin consists of "smooth" regions of poly-D-galactopyranosyluronic acid, and "hairy" regions. The latter regions consist of rhamnogalacturonan sequences that contain highly branched arabinogalactan side chains and galacturonan sequences with short side chains composed of D-xylose and mannose.

Because previous results suggested the presence of lactose-binding cell surface components on the tumor cells (38), applicant suggests that pectin which has highly branched arabinogalactan and galactorunan side chains expose a neutral sugar structure to the cell surface in the same mechanism as the asialofetuin. As a consequence, the motility of the tumor cells was experimentally prevented. When the mice were injected with tumor cells and pectin, the tumor size increased in the s.c. injection site probably as a participation phenomena of tumor cell surface lectin in cell-pectin-cell interaction, the pectin mediating cell to cell monotypic aggregation in vitro. That is, the unadulterated pectin promoted cell to cell contact and the formation of emboli thereby.

It is also possible that all surface lectins recognize and bind galactosyl residues from the neutral sugars on the side chains of the galacturonic acid. The circulating tumor emboli which was formed either by homotypic or heterotypic aggregation may be eliminated by host defenses. However, the rest of the tumor cells may be nonspecifically arrested in capillaries due to entrapment of large deformable cell emboli or they may be arrested specifically (43-44).

In the capillary bed of the organ, the metastasizing tumor cells are attached to the endothelial basement membranes and it is accepted that the extravasation process (43) is similar to cell invasion to the circulation system from a primary tumor. The role of carbohydrate residues in mediation of adhesion between cells was indicated also in reports on the ability of simple sugars to inhibit the aggregation of cells (20, 45, 22). Even though some simple sugars inhibit the aggregation in vitro (22), injection of galactose with tumor cells did not inhibit the aggregation of tumor cells, and failed to prevent the formation of colonies in lung.

The pectin, as a highly branched polymer sugar, was degraded sequentially as schematically illustrated in FIG. 6. In that degradation process of pectin two steps were involved; degradation of the main pectin polymer chain in a highly base condition by the elimination reaction which was described previously (46), and partial degradation of neutral sugars to the main three groups as shown in FIG. 6c.

The highly branched neutral sugar from pectin after short treatment with acid increased the homotypic aggregation of tumor cells and more nodules appeared in the lung, while the second group of degraded neutral sugar prevented the homotypic and heterotypic aggregation completely. This is consistent with the results of the aggregation experiments shown in FIGS. 8(A)-(D).

Applicant has shown that after a short treatment with acid, the highly branched neutral sugars from pectin increased the homotypic aggregation of the tumor cells in vivo as evidenced by the appearance of more nodules in the lungs (Table 2), while the second group of degraded neutral sugars probably prevented the homotypic and the heterotypic aggregation completely due to the total absence of lung nodules (FIG. 5, group B). It can be concluded that while unaltered pectin caused the formation of emboli and thereby increased metastatic lesions in the lung, the acid treated (B) MCP bound cell surface sites but because it lacks branching like the pectin, it did not form emboli. Rather, the (B) MCP inhibited the formation of emboli by taking up cell surface binding sites and preventing further cell to cell interaction of those sites. This is consistent with the results of the in vitro studies.

Hence, the presented date shows the modified pectin is capable of preventing tumor cell migration and cell to cell and cell to substratum interaction thereby inhibiting metastatic activity of malignant tumor cells.

What is claimed is:

1. A method for treating the metastasis of a tumor cell in an animal comprising:
   I. preparing a modified pectin by:
      a. providing a quantity of pectin, said pectin comprising a rhamnogalacturan backbone having side chains of neutral sugars dependent therefrom;
      b. maintaining the pectin at an alkaline pH for a time sufficient to disrupt the rhamnogalacturan backbone whereby a depolymerized pectin is obtained;
      c. maintaining the depolymerized pectin at an acidic pH for a time sufficient to break the side chains of neutral sugars into smaller units having an average molecular weight of 10.2 kd as determined by viscosity measurements at 26° C., whereby said modified pectin is obtained; and
   II. contacting said tumor cell with said modified pectin.

2. A method as in claim 1, wherein the step of providing a quantity of pectin comprises dissolving said pectin in a solvent to obtain a solution of pectin.

3. A method as in claim 2, wherein the step maintaining the pectin at an alkaline pH comprises maintaining the solution of pectin at a pH of at least 10.

4. A method as in claim 3, further comprising maintaining said solution of pectin at a pH of at least 10 for approximately 30 minutes.

5. A method as in claim 2, wherein the step of maintaining the depolymerized pectin at an acidic pH comprises maintaining the depolymerized pectin at a pH of approximately 3.

6. A method as in claim 5 wherein the depolymerized pectin is maintained at a pH of approximately 3 for 10 to 24 hours.

7. A method as in claim 1 wherein the step of preparing a modified pectin comprises the further step of neutralizing the modified pectin to a pH of approximately 6.3.

8. A method as in claim 7, comprising the further steps of washing and dehydrating the modified pectin so as to prepare a final solution comprising approximately 5-10% by weight of said weight of said modified pectin.

9. A method as in claim 1, wherein the step of contacting the tumor cell with the modified pectin comprises injecting the modified pectin into the animal.

10. A method for treating the metastasis of a melanoma cell in an animal comprising:
    I. preparing a modified pectin by:
       a. dissolving a quantity of pectin in a solvent, said pectin comprising a rhamnogalacturan backbone having side chains of neutral sugars dependent therefrom;
       b. maintaining the solution of pectin at an alkaline pH for a time sufficient to disrupt the rhamnogalacturan backbone, whereby a depolymerized pectin is obtained;
       c. maintaining the depolymerized pectin at an acidic pH for a time sufficient to break the side chains of neutral sugars into smaller units having an average molecular weight of 10.2 kd as determined by viscosity measurements at 26° C., whereby said modified pectin is obtained; and
    II. contacting said melanoma cell with said modified pectin.

* * * * *